United States Patent
Xie (12)

(10) Patent No.: US 11,452,888 B2
(45) Date of Patent: Sep. 27, 2022

(54) COMBINATION FACE MASK AND AIR FILTER WITH UV LAMP

(71) Applicant: Qingbo Xie, Guangdong (CN)

(72) Inventor: Qingbo Xie, Guangdong (CN)

(73) Assignee: Shenzhen Aurora Technology Limited, Shenzhen (CN)

( * ) Notice: Subject to any disclaimer, the term of this patent is extended or adjusted under 35 U.S.C. 154(b) by 196 days.

(21) Appl. No.: 16/929,129

(22) Filed: Jul. 15, 2020

(65) Prior Publication Data
US 2020/0346050 A1    Nov. 5, 2020

(51) Int. Cl.
| | | |
|---|---|---|
| A62B 7/00 | (2006.01) |
| A62B 7/10 | (2006.01) |
| A61L 9/20 | (2006.01) |
| A62B 9/00 | (2006.01) |
| A62B 23/02 | (2006.01) |
| A62B 18/02 | (2006.01) |

(52) U.S. Cl.
CPC .............. *A62B 7/10* (2013.01); *A61L 9/20* (2013.01); *A62B 9/00* (2013.01); *A62B 18/025* (2013.01); *A62B 23/02* (2013.01); *A61L 2209/12* (2013.01); *A61L 2209/14* (2013.01)

(58) Field of Classification Search
CPC ..... A61L 7/10; A61L 9/20; A61L 9/00; A61L 18/025; A61L 23/02; A61L 2209/12; A61L 2209/14; A62B 7/10; A62B 18/025; A62B 23/02
See application file for complete search history.

(56) References Cited

U.S. PATENT DOCUMENTS

| | | | | |
|---|---|---|---|---|
| 5,505,904 | A * | 4/1996 | Haidinger | A61L 9/20 422/4 |
| 8,017,073 | B2 * | 9/2011 | Engelhard | A61L 9/00 422/24 |
| 10,905,791 | B1 * | 2/2021 | Caballero | A61L 9/20 |
| 2008/0279731 | A1 * | 11/2008 | Goreham | A61L 9/037 422/123 |
| 2010/0307332 | A1 * | 12/2010 | Yuen | B03C 3/383 96/25 |
| 2011/0126828 | A1 * | 6/2011 | Wu | B03C 3/155 128/205.12 |
| 2021/0275838 | A1 * | 9/2021 | Goswami | A62B 18/025 |

* cited by examiner

*Primary Examiner* — Steven O Douglas

(57) ABSTRACT

A combination face mask and air filter includes a face mask; an air filter including a centrifugal fan, a circuit board, a filter element, a power supply, a housing for enclosing the centrifugal fan, the circuit board, the filter element, and the power supply, a cover releasably secured to the housing, and a UV lamp; a tube having a first end attached to the face mask; and a strap having two ends attached to the housing. The centrifugal fan includes an inlet and an outlet. The UV lamp is disposed at the outlet of the centrifugal fan. A second end of the tube passes through the housing to communicate with the outlet of the centrifugal fan.

1 Claim, 6 Drawing Sheets

COMBINATION FACE MASK AND AIR FILTER WITH UV LAMP

BACKGROUND OF THE INVENTION

1. Field of the Invention

The invention relates to face coverings and more particularly to a combination face mask and air filter having an ultraviolet (UV) lamp.

2. Description of Related Art

A face mask (also known as a surgical mask) is intended to be worn by health professionals during healthcare procedures. It is designed to prevent infections in patients and treating personnel by catching bacteria shed in liquid droplets and aerosols from the wearer's mouth and nose. With respect to some infections like influenza they appear as effective as respirators.

Face masks vary by quality and levels of protection. Face masks may be labeled as surgical, isolation, dental, or medical procedure masks. Chinese health officials distinguish between medical (non-surgical) and surgical masks. Face masks are made of a nonwoven fabric created using a melt blowing process. Face masks are popularly worn by the general public all year round in East Asian countries like China, Japan and South Korea to reduce the chance of spreading airborne diseases to others, and to prevent the breathing in of airborne dust particles created by air pollution.

However, conventional face masks are made from paper or other non-woven material and are discarded after each use (i.e., being not washable or reusable). Further, its ventilation is poor with foul air being incompletely expelled from inside of the face mask, and thus the desired fresh air inhaled by a wearer is compromised.

Thus, the need for improvement still exists.

SUMMARY OF THE INVENTION

The invention has been made in an effort to solve the problems of the conventional art including poor ventilation, incomplete foul air exit, and not quite fresh air being inhaled by a wearer by providing a combination face mask and air filter having a UV lamp with novel and nonobvious characteristics.

To achieve above and other objects of the invention, the invention provides a combination face mask and air filter comprising a face mask; an air filter including a centrifugal fan, a circuit board, a filter element, a power supply, a housing for enclosing the centrifugal fan, the circuit board, the filter element, and the power supply, a cover releasably secured to the housing, and an ultraviolet (UV) lamp; a tube having a first end attached to the face mask; and a strap having two ends attached to the housing; wherein the centrifugal fan includes an inlet and an outlet; wherein the UV lamp is disposed at the outlet of the centrifugal fan; and wherein a second end of the tube passes through the housing to communicate with the outlet of the centrifugal fan.

Preferably, the second end of the tube is formed as a connector attached to the housing for communicating with the outlet of the centrifugal fan.

Preferably, filter element is disposed at the inlet of the centrifugal fan.

Preferably, the circuit board includes a circular opening aligned with the inlet of the centrifugal fan; wherein the cover is aligned with the filter element; and wherein the filter element is aligned with the circular opening of the circuit board.

Preferably, further comprises a wall in the housing for separating the centrifugal fan from the power supply.

Preferably, further comprises a power socket on the housing, the power socket being electrically connected to the power supply.

Preferably, further comprises a push-button on the housing adjacent to the power socket, the push-button being electrically connected to the circuit board.

Preferably, wherein the cover includes a plurality of louvers aligned with the filter element.

Preferably, the housing further comprises two opposite clasps attached to two ends of the strap respectively.

Preferably, the ends of the straps are adjustably attached to the clasps.

The invention has the following advantageous effects in comparison with the prior art: clean air provided by the air filter, moisture and excessive heat removal, a degree of freshness and comfort on the face of a wearer, the UV light being capable of inactivating bacteria, viruses, and protozoa, and cleanliness of the face mask can be maintained for a prolonged period of time because the clean air drawn into the face mask can completely force foul air out of inside of the face mask, i.e., the face mask being durable.

The above and other objects, features and advantages of the invention will become apparent from the following detailed description taken with the accompanying drawings.

DETAILED DESCRIPTION OF THE INVENTION

Figure 1:
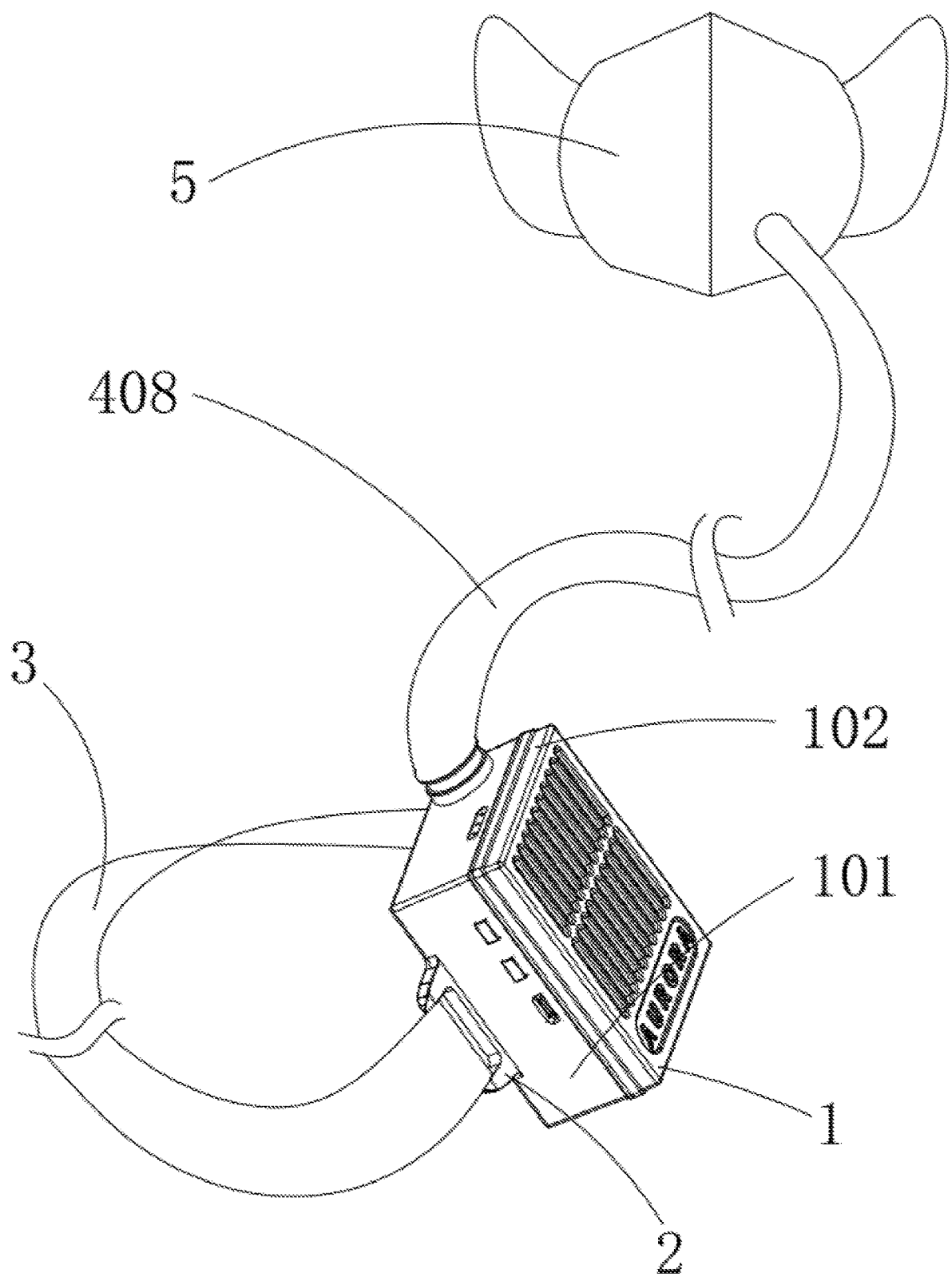
FIG. 1 is a perspective view of a combination face mask and air filter according to the invention.
Figure 2:
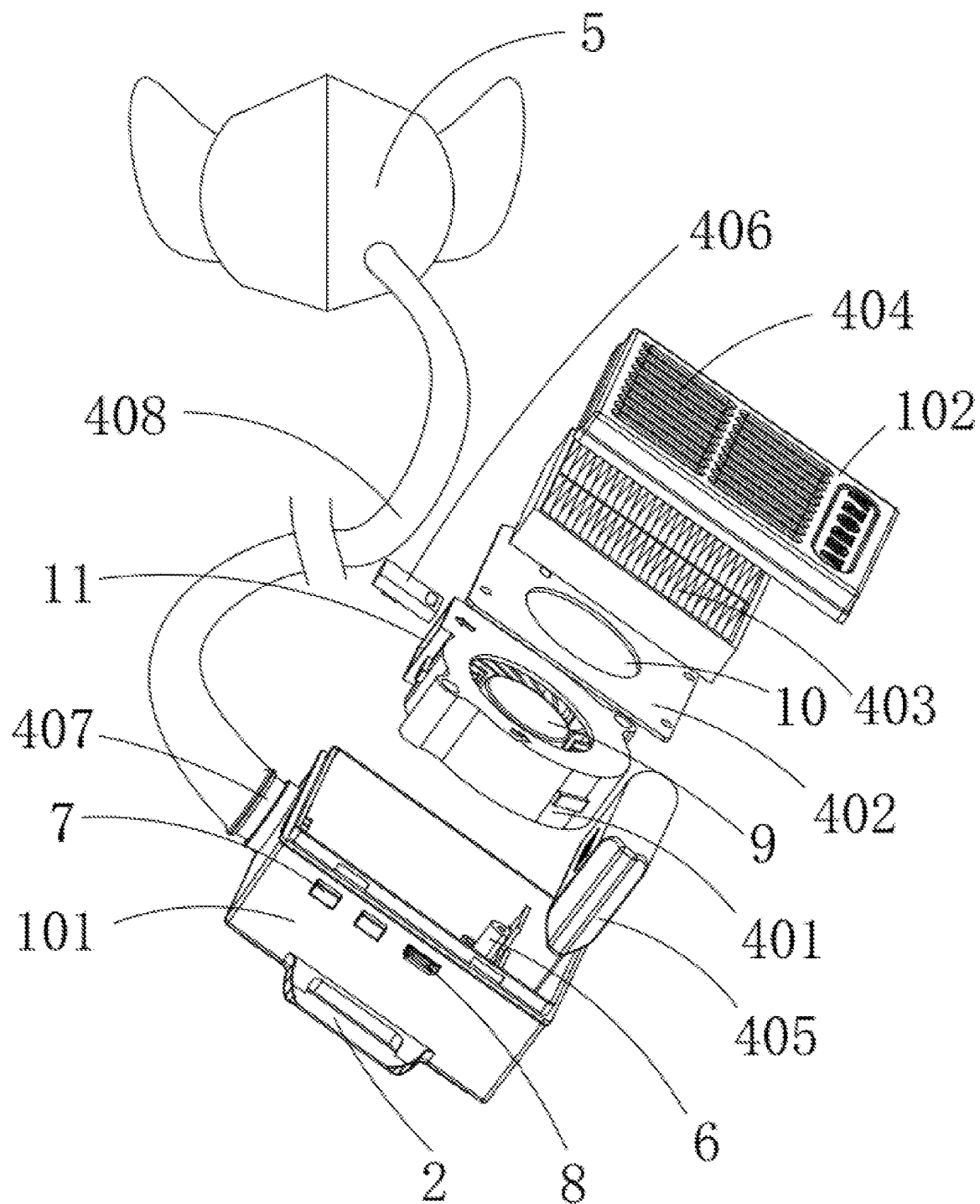
FIG. 2 is a perspective exploded view of the combination face mask and the air filter.

Referring to FIGS. 1 to 4B, a combination face mask and air filter in accordance with the invention comprises a face mask 5, a tube 408, a strap 3 and an air filter 1 as discussed in detail below.

The air filter 1 includes a centrifugal fan 401, a circuit board 402 for control purposes, a filter element 403, a power supply (e.g., rechargeable battery) 405, a housing 101 for enclosing the above components, and a cover 12 releasably secured to the housing 101.

The centrifugal fan 401 includes an inlet 9 and an outlet 11. The filter element 403 is disposed at the inlet 9 of the centrifugal fan 401. An ultraviolet (UV) lamp 406 is disposed at the outlet 11 of the centrifugal fan 401 and is electrically connected to the circuit board 402. A first end of the tube 408 is connected to the face mask 5. A second end of the tube 408 is formed as a connector 407 attached to the housing 101 so that the tube 408 may communicate with the outlet 11 of the centrifugal fan 401. The strap 3 has two ends attached to two clasps 2 on the housing 101 respectively. A circular opening 10 is provided through the circuit board 402 and aligned with the inlet 9 of the centrifugal fan 401 so that fresh air produced by the centrifugal fan 401 may pass through the opening 10. The cover 12 is aligned with the filter element 403 which in turn is aligned with the circuit board 402. The filter element 403 can remove solid particulates such as dust, pollen, mold, and bacteria from the air.

A wall 6 is provided in the housing 101 so that the centrifugal fan 401 can be disposed at an area adjacent to one side of the wall 6 and the power supply 405 can be disposed at an area adjacent to the other side of the wall 6 respectively. The power supply 405 is used to supply electricity to all components of the air filter 1.

In addition, a power socket 8 is provided on an outer surface of the housing 101. Mains power may be supplied to the power supply 405 for charging by inserting an end of a power cord into the power socket 8. The centrifugal fan 401 is electrically connected to the power supply 405. A push-button 7 and a power-on light (no numbered) are provided on the outer surface of the housing 101 adjacent to the power socket 8. The push-button 7 and a power-on light are electrically connected to the circuit board 402. A pressing of the push-button 7 may activate the air filter 1. The power-on light may light when the power supply 405 is activated.

Figure 4:
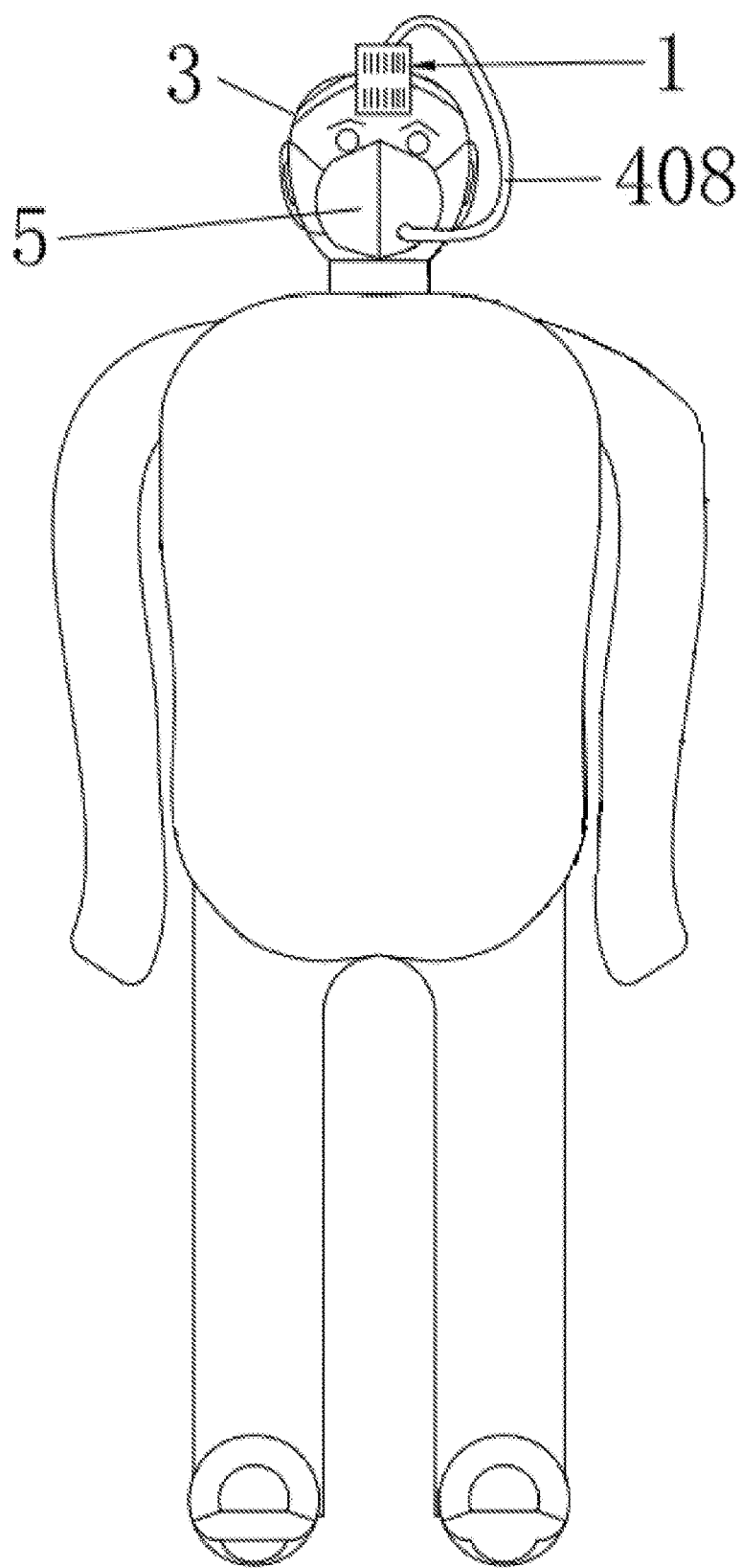
FIG. 4 schematically depicts a first preferred embodiment of the combination face mask and the air filter where the air filter is mounted on the forehead.
Figure 4A:
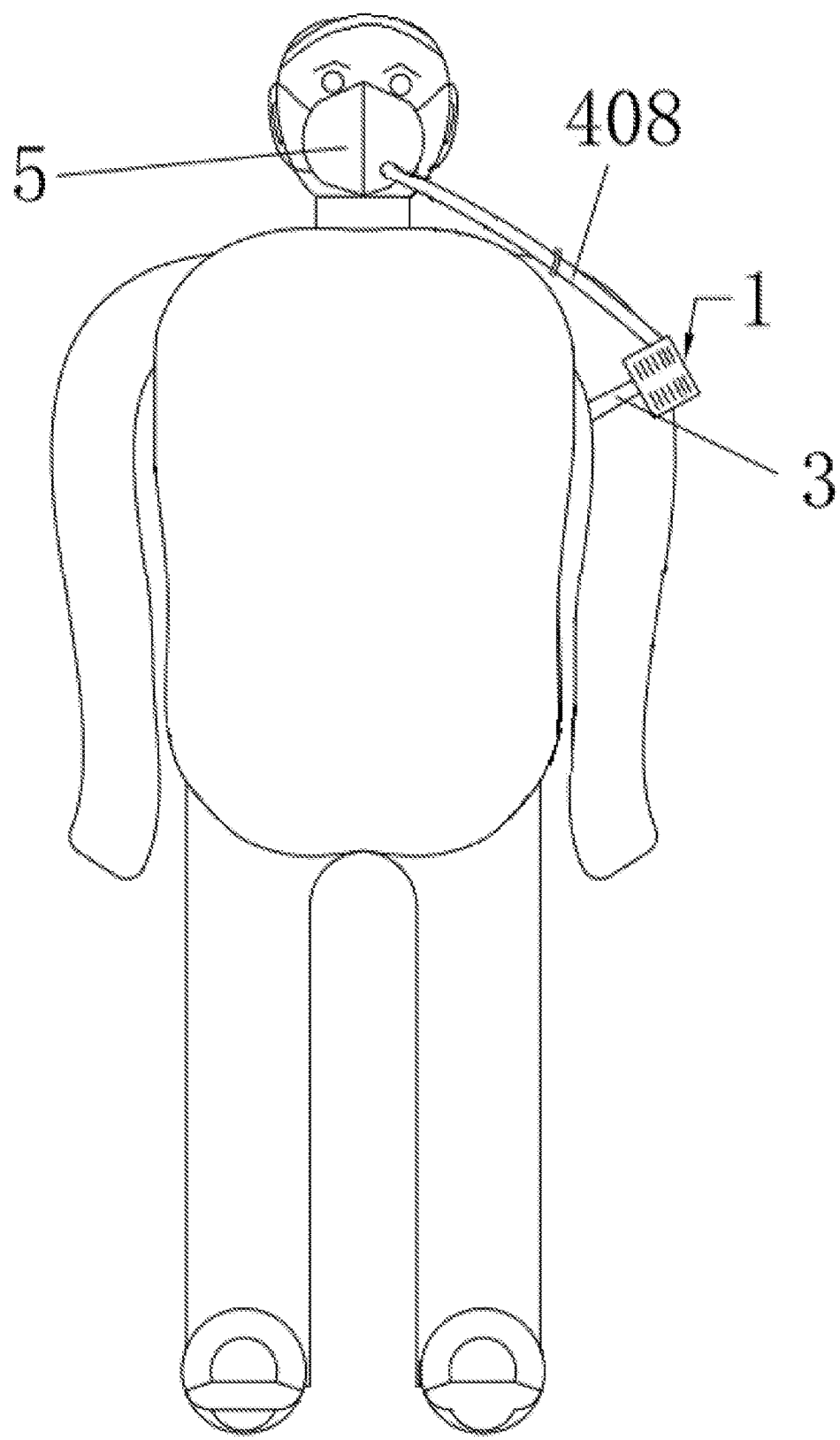
FIG. 4A schematically depicts a second preferred embodiment of the combination face mask and the air filter where the air filter is mounted on the arm.
Figure 4B:
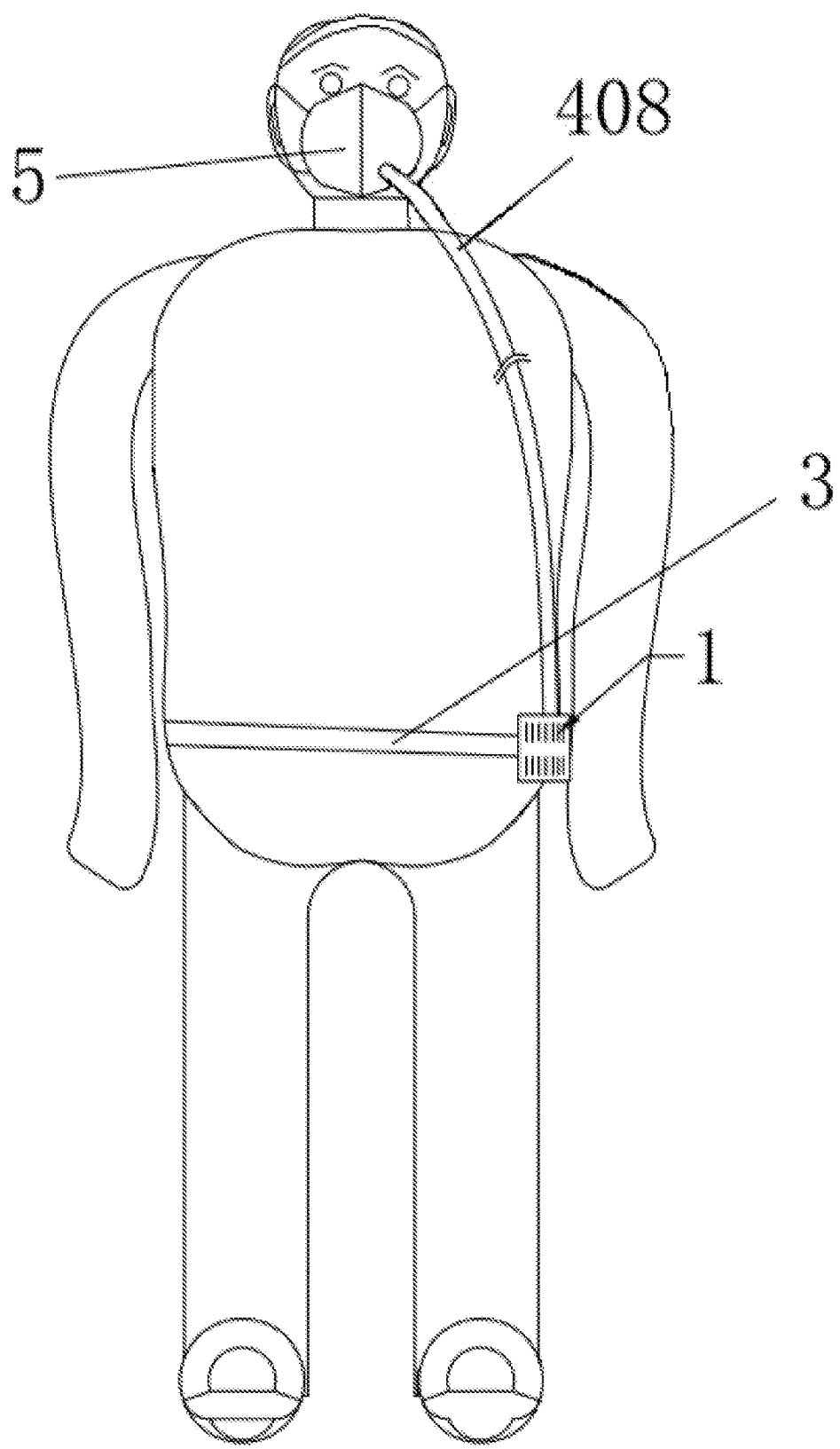
FIG. 4B schematically depicts a third preferred embodiment of the combination face mask and the air filter where the air filter is mounted on the waist.

The activated UV lamp 406 produces UV light which can inactivate bacteria, viruses, and protozoa. The activation of the UV lamp 406 can be controlled by pressing the push-button 7. Louvers 404 are provided on the cover 12 and aligned with the filter element 403 for bringing fresh air to the inlet 9 of the centrifugal fan 401. In use a person may adjust the strap 3 when the air filter 1 is worn on the forehead (FIG. 4), the arm (FIG. 4A) or the waist (FIG. 4B) until a degree of comfort is felt by the person.

An operation of the invention is discussed in detail below. A person (e.g., medical employee) may put the face mask 5 on his or her face and then put the air filter 1 on the forehead (FIG. 4), the arm (FIG. 4A) or the waist (4B). The employee may press the push-button 7 to activate the circuit board 402 which in turn activates the centrifugal fan 401 to draw air through the louvers 404 and the filter element 403 which removes solid particulates such as dust, pollen, mold, and bacteria from the air. The activated UV lamp 406 at the outlet 11 of the centrifugal fan 401 produces UV light which can inactivate bacteria, viruses, and protozoa. The pressurized clean air flows to the face mask 5 through the tube 408. And in turn, the pressurized clean air forces moisture and excessive heat out of the face mask 5 through other portions of the face mask 5 (i.e., portions other than an air inlet of the face mask 5 in FIG. 3). As a result, the employee may feel a degree of freshness and comfort on his or her eyes.

Figure 3:
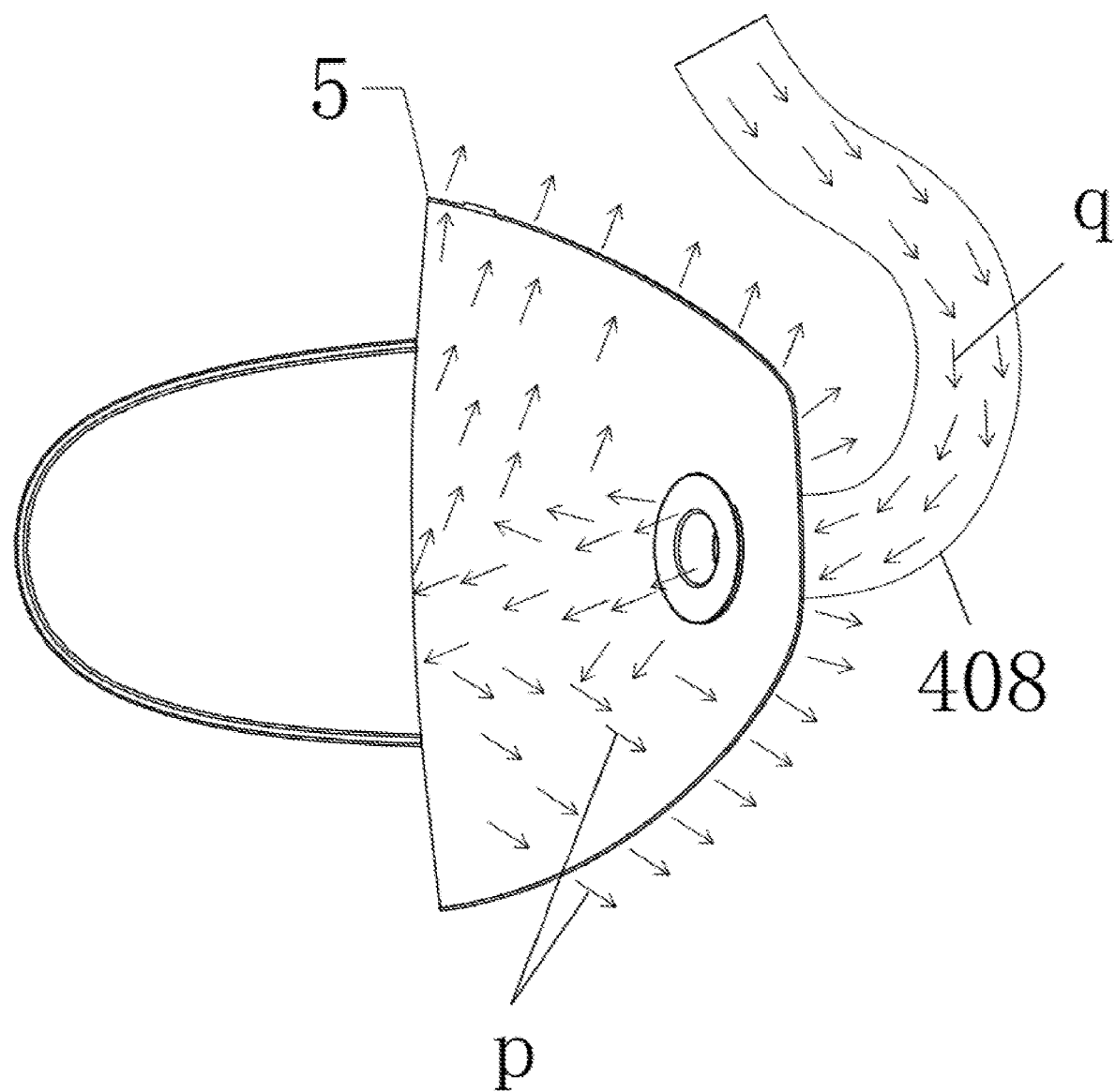
FIG. 3 schematically depicts air flow through the face mask.

As shown in FIG. 3 specifically, the pressurized clean air q continuously flows to the face mask 5 through the tube 408. And in turn, the pressurized clean air forces foul air p between the face and the face mask 5 out of the face mask 5 (i.e., expelling air from inside of the face mask 5).

The invention has the following advantageous effects in comparison with the prior art: clean air provided by the air filter 1, moisture and excessive heat removal, a degree of freshness and comfort on the face of a wearer, the UV light being capable of inactivating bacteria, viruses, and protozoa, and cleanliness of the face mask 5 can be maintained for a prolonged period of time because the clean air drawn into the face mask 5 can completely force foul air out of inside of the face mask 5, i.e., the face mask 5 being durable.

While the invention has been described in terms of preferred embodiments, those skilled in the art will recognize that the invention can be practiced with modifications within the spirit and scope of the appended claims.

What is claimed is:
1. A combination face mask and air filter comprising:
a face mask;
an air filter including a centrifugal fan, a circuit board, a filter element, a power supply, a housing for enclosing the centrifugal fan, the circuit board, the filter element, and the power supply, a cover releasably secured to the housing, and an ultraviolet lamp;
a tube having a first end attached to the face mask; and
a strap having two ends attached to the housing;
wherein the centrifugal fan includes an inlet and an outlet;
wherein the ultraviolet lamp is disposed at the outlet of the centrifugal fan;
wherein a second end of the tube passes through the housing to communicate with the outlet of the centrifugal fan;
wherein the circuit board includes a circular opening aligned with the inlet of the centrifugal fan;
wherein the cover is aligned with the filter element; and
wherein the filter element is aligned with the circular opening of the circuit board.

* * * * *